(12) United States Patent
Son

(10) Patent No.: US 7,842,315 B2
(45) Date of Patent: Nov. 30, 2010

(54) COMPOSITIONS FOR TREATING LIVER FIBROSIS OR CIRRHOSIS

(75) Inventor: Chang Gue Son, Daejeon (KR)

(73) Assignee: Daejeon University, Daejeon (KR)

( * ) Notice: Subject to any disclaimer, the term of this patent is extended or adjusted under 35 U.S.C. 154(b) by 509 days.

(21) Appl. No.: 11/872,696

(22) Filed: Oct. 15, 2007

(65) Prior Publication Data

US 2008/0260870 A1    Oct. 23, 2008

(30) Foreign Application Priority Data

Apr. 9, 2007    (KR)    .................. 10-2007-0034709

(51) Int. Cl.
| | |
|---|---|
| A61K 36/00 | (2006.01) |
| A61K 36/076 | (2006.01) |
| A61K 36/9064 | (2006.01) |
| A61K 36/484 | (2006.01) |
| A61K 36/282 | (2006.01) |
| A61K 36/537 | (2006.01) |

(52) U.S. Cl. .................. 424/725; 424/740; 424/746; 424/776; 424/777; 424/773

(58) Field of Classification Search .................. None
See application file for complete search history.

(56) References Cited

U.S. PATENT DOCUMENTS 6,126,942 A * 10/2000 Yang .......................... 424/728
2003/0152652 A1 * 8/2003 Baker et al. .................. 424/737

FOREIGN PATENT DOCUMENTS

| CN | 1277050 A | * | 12/2000 |
| CN | 1698877 A | * | 11/2005 |
| KR | 2004079724 A | * | 9/2004 |
| KR | 10-2005-0100746 A | | 10/2005 |
| KR | 10-2005-50116007 A | | 12/2005 |
| KR | 10-2006-0104405 A | | 10/2006 |

OTHER PUBLICATIONS

Silva Anderson Soares da et al, Chronic liver disease prevention strategies and liver transplantation, Acta Cirurgica Brasilera/Sociedade Brasileira pera Desenvolvimento Pesquisa em Cirurgia, (2006) vol. 21 Suppl 1, pp. 79-84. Ref: 29.*
Definition of cirrhosis from Merck manual, accessed on Feb. 22, 2010, pp. 1-4.*
Brind et al, Prevalence and pattern of familial disease in primary biliary cirrhosis, Gut, (Apr. 1995) vol. 36, No. 4, pp. 615-617.*
Hung et al, Biochemical characterization of the Wilson disease protein and functional expression in the yeast *Saccharomyces cerevisiae*, The Journal of biological chemistry, (Aug. 22, 1997) vol. 272, No. 34, pp. 21461-21466.*
Ohbayashi, Considerations on familial clustering of liver cirrhosis and hepatocellular carcinoma Gan to kagaku ryoho. Cancer & chemotherapy, (May 1982) vol. 9, No. 5, pp. 799-807.*
Twedt et al, Clinical, morphologic, and chemical studies on copper toxicosis of Bedlington Terriers, Journal of the American Veterinary Medical Association, (1979) vol. 175, No. 3, pp. 269-275.*
Sur et al, Indian childhood cirrhosis: an inherited disorder of tryptophan metabolism? British medical journal, (Aug. 19, 1978) vol. 2, No. 6136, pp. 529-531.*

* cited by examiner

*Primary Examiner*—Qiuwen Mi
(74) *Attorney, Agent, or Firm*—Lee, Hong, Degerman, Kang & Waimey

(57) ABSTRACT

Disclosed is a composition for hepatoprotection, or for prevention or treatment of liver fibrosis or cirrhosis, which comprises as an active ingredient a water extract of a mixture of *Trionycis Carapax, Raphani Semen, Artemisia capillaris* Herba, *Atractylodis Macrocephalae* Rhizoma, *Poria cocos, Alismatis* Rhizoma, *Atractylodis* Rhizoma, *Salvia Miltiorrhizae* Radix, *Polyporus, Amomi Fructus, Ponciri Fructus, Glycyrrhizae* Radix and *Helenii* Radix.

5 Claims, 7 Drawing Sheets

COMPOSITIONS FOR TREATING LIVER FIBROSIS OR CIRRHOSIS

CROSS-REFERENCE TO RELATED APPLICATIONS

Pursuant to 35 U.S.C. §119(a), this application claims the benefit of earlier filing date and right of priority to Korean Application No. 10-2007-0034709, filed on Apr. 9, 2007, the contents of which are hereby incorporated by reference herein in their entirety.

TECHNICAL FIELD

The present invention relates to an herbal composition having hepatoprotective effect, or having preventive or therapeutic effect on liver fibrosis or cirrhosis. More specifically, the invention relates to the composition for protecting liver cells, and for restraining and treating the development of liver fibrosis or cirrhosis caused by liver damage, which comprises as an active ingredient, a water extract of a mixture of 13 specific herbal medicines.

BACKGROUND ART

Considering various patterns and progresses of liver diseases, it is very important in the clinical therapy to inhibit the development of fibrosis or cirrhosis or to inhibit the progress of cirrhosis if already developed. So, most researchers studying on treatment of liver diseases have tried to develop preventives or therapeutics for cirrhosis. Nevertheless, satisfactory therapies or therapeutics have not been developed yet.

Continuous liver cell destruction caused by excessive alcohol consumption or toxic substances, or by chronic viral hepatitis leads to decrease in the number of liver cells which constitute liver tissue, and transformation of Ito cells into fibroblasts. Theses processes thereby result in the increase of connective tissue fibers inside liver. Therefore, Inhibition of fibroblastic activation or the fibrotic formation is critical for preventing or treating cirrhosis or in developing a drug. Recently, excessive generation of reactive oxygen species (ROS) and deficiency of their scavenging system such as glutathione system, superoxide dismutase (SOD) or catalase have been reported to elicit and accelerate fibrotic process in the liver. It is known that these conditions can be examined by oxidizing molecules within cells including cell membranes, and then, measuring the level of lipid peroxidation. It is also known that inflammation-related genes such as tumor necrosis factor-alpha (TNF-$\alpha$), inducible nitric oxide synthase (iNOS) and transforming growth factor-beta (TGF-$\beta$) play crucial roles in cell destruction and fibrosis.

Various kinds of single medicines like silymarin extracted from an herbal medicine and combined medicines like Shosaiko-to (Xiao-Cai-hu-Tang) prepared by decoction of *Bupleurum falcatum* L., Scutellariae Radix, ginseng, *Pinellia ternata*, liquorice, ginger and *Zizyphus jujuba* Miller are known to protect liver cells and to suppress the lipid peroxidation or the expression of inflammation-related genes, and thus, have been widely used in clinical therapy. However, theses drugs show some effectiveness on the improvement of inflammation in liver, but cannot significantly inhibit the progress of liver fibrosis or cirrhosis. Furthermore, liver cirrhosis, an extremely complicated process, is believed to involve many pathological factors, and thus, it is expected to develop a more effective drug by modifying a combined medicine of oriental medicine accumulated from long-time clinical therapies with conducting modern scientific experiments.

Korean Patent Publication No. 2005-100746 discloses an extract for inhibiting liver fibrosis obtained by extracting an herbal mixture of *Artemisia capillaris* Herba, Atractylodis Rhizoma, *Magnoliae officinalis, Aurantii nobilis* Pericarpium, Polyporus, Alismatis Rhizoma, *Atractylodis Macrocephalae* Rhizoma, *Poria cocos, Raphani Semen, Zingiber officinale* Roscoe, *Pinellia ternata, Areca catechu,* Sparganii Rhizoma, Zedoariae Rhizoma and Aurantii pericarpium with hot water, and a pharmaceutical composition comprising the same. Korean Patent Publication No. 2005-116007 discloses a pharmaceutical composition for preventing and treating liver diseases essentially containing an extract of *Artemisia capillaris* Herba, *Atractylodis Macrocephalae* Rhizoma, *Coriolus versicolor, Orostachys japonicus* and Polyporus. Korean Patent Publication No. 2006-104405 discloses an herbal extract for preventing and treating liver fibrosis prepared by extracting with a solvent a mixed powder of 17 herbal medicines comprising 3~5 parts by weight of *Euonymus alatus,* 3~5 parts by weight of oyster shell powder, 3~5 parts by weight of Ampelopsis radix, 3-5 parts by weight of white grub, 1~3 parts by weight of *Artemisia capillaris* Herba, 1-3 parts by weight of Alismatis Rhizoma, 1~3 parts by weight of *Bufonis venenum,* 1~3 parts by weight of Rhizomes of *Belamcanda chinensis,* 0.5~1.5 parts by weight of *Polygonum aviculare* Linne, 0.5~1.5 parts by weight of *Raphani Semen,* 0.5~1.5 parts by weight of *Curcuma Longa,* 0.5~1.5 parts by weight of Black Cohosh, 0.5~1.5 parts by weight of *Poria cocos,* 0.5~1.5 parts by weight of *Eriobotryae folium,* 0.5~1.5 parts by weight of Glycyrrhizae Radix, 0.1~1 parts by weight of *Lepidium apetalum,* and 0.1~1 part by weight of heat-treated alumen. However, these compositions are composed of different components from that of the present invention containing 13 herbal medicines. They have been alleged to have therapeutic effect on liver fibrosis, but still need to be improved in view of effects.

DISCLOSURE OF THE INVENTION

The present inventors extensively studied and conducted experiments on herbal medicines having various compositions with liver cirrhosis animal models induced by chronic liver cell destruction. As a result, the present inventors confirmed that a water extract of a mixture of 13 herbal medicines has excellent preventive and therapeutic effects on liver fibrosis.

Therefore, it is an object of the present invention to provide a novel herbal composition having hepatoprotective effect or having preventive or therapeutic effect on liver fibrosis or cirrhosis.

The present invention relates to a composition for hepatoprotection, or for prevention or treatment of liver fibrosis or cirrhosis, which comprises as an active ingredient a water extract of a mixture of *Trionycis Carapax, Raphani Semen, Artemisia capillaris* Herba, *Atractylodis Macrocephalae* Rhizoma, *Poria cocos,* Alismatis Rhizoma, Atractylodis Rhizoma, *Salvia Miltiorrhizae* Radix, Polyporus, Amomi Fructus, Ponciri Fructus, Glycyrrhizae Radix and Helenii Radix.

In a preferable embodiment, the mixture comprises 2.5~7.5 parts by weight of *Trionycis Carapax,* 2.5~7.5 parts by weight of *Raphani Semen,* 2.5~7.5 parts by weight of *Artemisia capillaris* Herba, 1.5~4.5 parts by weight of *Atractylodis Macrocephalae* Rhizoma, 1.5~4.5 parts by weight of *Poria cocos,* 1.5~4.5 parts by weight of Alismatis Rhizoma, 1.5~4.5 parts by weight of Atractylodis Rhizoma, 1.5~4.5 parts by weight of *Salvia Miltiorrhizae* Radix, 1~3 parts by weight of Polyporus, 1~3 parts by weight of Amomi Fructus, 1~3 parts by weights of Ponciri Fructus, 0.5~1.5 parts by weight of Glycyrrhizae Radix, and 0.5~1.5 parts by weight of Helenii Radix. In the most preferable embodiment, the mixture contains 5 parts by weight of *Trionycis Carapax,* 5 parts by weight of *Raphani Semen,* 5 parts by weight of *Artemisia capillaris* Herba, 3 parts by weight of *Poria cocos,* 3 parts by weight of Alismatis Rhizoma, 3 parts by weight of *Atractylodis Macrocephalae* Rhizoma, 3 parts by weight of Atractylodis Rhizoma, 3 parts by weight of *Salvia Miltiorrhizae* Radix, 2 parts by weight of Polyporus, 2 parts by weight of Amomi Fructus, 2 parts by weight of Ponciri Fructus, 1 part by weight of Glycyrrhizae Radix and 1 part by weight of Helenii Radix.

The composition of the present invention can comprise any pharmaceutically or food-engineeringly acceptable carrier, in addition to the above active ingredient. The composition of the present invention can be used as a medicine, a health food or a heath supplement food for hepatoprotection, or for prevention or treatment of liver fibrosis or cirrhosis.

Hereinafter, the present invention will be described in detail.

*Trionycis Carapax,* the 1$^{st}$ herbal medine used for the present invention, indicates the theca of a soft-shelled turtle, and is used as an antipyretic and a tonic.

*Raphani Semen,* the 2$^{nd}$ herbal medicine used for the present invention, has effects of making vital energy (qi) pass through and relieving indigestion, and so it can be used for abdominal dropsy, eructation, hyperacidity and diarrhea. In addition, it is useful for calming down vital energy, diluting phlegm, relieving cough, asthma and constipation, treating anorexia, and stopping old phlegm and cough.

*Artemisia capillaris* Herba, the 3$^{rd}$ herbal medicine used for the present invention, is used for symptoms of fuming, systemic yellow, and red and little urine in jaundice caused by wet fever, that is, acute hepatitis. It is also used for chronic hepatitis, liver cirrhosis, liver cancer, cholecystitis, gallstones, as well as for skin disorders including eczema, ascariasis, trichophytia and rubella, and high fever and craziness caused by epidemic diseases.

*Atractylodis Macrocephalae* Rhizoma, the 4$^{th}$ herbal medicine used for the present invention, is beneficial for little eating, bore, yellow face and dilute stool or diarrhea from weakness of the spleen and the stomach, and helps moisture excretion for systemic swelling and indigestion from moisture congestion. It is also used for excessive heart beats, cough, thin sputum, etc., caused by retention of fluid from accumulation of water and moisture in the spleen, spontaneous sweating in skin caused by weakness of splenetic energy, and vomiting of pregnancy. If is also used for cold with gastrointestinal disorders, and limb pain.

*Poria cocos,* the 5$^{th}$ herbal medicine used for the present invention, has been used as a tonic for a long time ago. It protects the spleen by acting on lung meridian, spleen meridian, heart meridian, kidney meridian, bladder meridian, etc., dilutes phlegm, and has tranquilizing effect.

Alismatis Rhizoma, the 6$^{th}$ herbal medicine used for the present invention, is used as a diuretic and a therapeutic for hydrops and gonorrhea.

Atractylodis Rhizoma, the 7$^{th}$ herbal medicine used for the present invention, is known to have sweating, diuretic, analgesic and stomach strengthening activity, and thus, it is used for anorexia, indigestion, gastroenteritis, cold and the like. Salvia Miltiorrhizae Radix, the 8$^{th}$ herbal medicine used for the present invention, is used for menstrual disorder, menstrual pain and postpartum abdominal pain of women, deep abdominal pain caused by extravasated blood, bruise, insomnia, skin rash and the like.

Polyporus, the 9$^{th}$ herbal medicine used for the present invention, has been used as a diuretic in the oriental medicine.

Amomi Fructus, the 10$^{th}$ medical herb component used for the present invention, is used for nausea, abdominal pain, diarrhea and epigastric pain caused by invasion of moisture to the spleen and the stomach, and makes stomach strong by helping flow of vital energy.

Ponciri Fructus, the 11$^{th}$ herbal medicine used for the present invention, is used as an aromatic bitter stomachic.

Glycyrrhizae Radix, the 12$^{th}$ herbal medicine used for the present invention, sweetens bitterness of a medicine so that it can be easily taken, removes toxicity of all medicines, relieves cough and phlegm, and neutralizes all medicines.

Helenii Radix, the 13$^{th}$ herbal medicine used for the present invention, is used as a diaphoretic, a diuretic and an expectorant, and has an anthelmintic ingredient.

The active ingredient of the composition according to the present invention is a water, particularly, hot water, extract, of a mixture of *Trionycis Carapax, Raphani Semen, Artemisia capillaris* Herba, *Atractylodis Macrocephalae* Rhizoma, *Poria cocos,* Alismatis Rhizoma, Atractylodis Rhizoma, *Salvia Miltiorrhizae* Radix, Polyporus, Amomi Fructus, Ponciri Fructus, Glycyrrhizae Radix and Helenii Radix, preferably of 2.5~7.5 parts by weight of *Trionycis Carapax,* 2.5~7.5 parts by weight of *Raphani Semen,* 2.5~7.5 parts by weight of *Artemisia capillaris* Herba, 1.5~4.5 parts by weight of *Atractylodis Macrocephalae* Rhizoma, 1.5~4.5 parts by weight of *Poria cocos,* 1.5~4.5 parts by weight of Alismatis Rhizoma, 1.5~4.5 parts by weight of Atractylodis Rhizoma, 1.5~4.5 parts by weight of *Salvia Miltiorrhizae* Radix, 1~3 parts by weight of Polyporus, 1~3 parts by weight of Amomi Fructus, 1~3 parts by weight of Ponciri Fructus, 0.5~1.5 parts by weight of Glycyrrhizae Radix, and 0.5~1.5 parts by weight of Helenii Radix, and most preferably, of 5 parts by weight of *Trionycis Carapax,* 5 parts by weight of *Raphani Semen,* 5 parts by weight of *Artemisia capillaris* Herba, 3 parts by weight of *Poria cocos,* 3 parts by weight of Alismatis Rhizoma, 3 parts by weight of *Atractylodis Macrocephalae* Rhizoma, 3 parts by weight of Atractylodis Rhizoma, 3 parts by weight of *Salvia Miltiorrhizae* Radix, 2 parts by weight of Polyporus, 2 parts by weight of Amomi Fructus, 2 parts by weight of Ponciri Fructus, 1 part by weight of Glycyrrhizae Radix and 1 part by weight of Helenii Radix.

In the present invention, for example, the mixture of 5 parts by weight of *Trionycis Carapax,* 5 parts by weight of *Raphani Semen,* 5 parts by weight of *Artemisia capillaris* Herba, 3 parts by weight of *Atractylodis Macrocephalae* Rhizoma, 3 parts by weight of *Poria cocos,* 3 parts by weight of Alismatis Rhizoma, 3 parts by weight of Atractylodis Rhizoma, 3 parts by weight of *Salvia Miltiorrhizae* Radix, 2 parts by weight of Polyporus, 2 parts by weight of Amomi Fructus, 2 parts by weight of Ponciri Fructus, 1 parts by weight of Glycyrrhizae Radix and 1 parts by weight of Helenii Radix is decocted with distilled water, and the decoction is filtered, centrifuged and lyophilized to obtain a dried extract.

The composition ratios of the above herbal medicines were derived from repeated experiments. If the ratio of each herbal medicine is lower than the above lower limit, the pharmacological effect of the medicine may be decreased. On the contrary, if the ratio of each herbal medicine is higher than the above upper limit, the pharmacological effects of other medicines may be decreased to deteriorate synergistic and cooperative effects of the composition. Therefore, the above composition ratios are preferable. However, the composition ratios are only preferable ones, and so can be adjusted by those skilled in the art in a suitable manner as long as they do not have adverse effects on pharmacological effects of the present composition. Therefore, the present invention is not specially limited by the above composition ratios.

The composition of the present invention significantly improves bilirubin metabolic capability of the liver and liver cell damage, effectively inhibits lipid peroxidation, fibrosis and cirrhosis of liver tissue, and suppresses the expression of genes involved in liver inflammation and fibrosis.

The composition of the present invention can be manufactured into a pharmaceutical formulation by mixing the active ingredient with one or more pharmaceutically acceptable carriers. Depending on the purpose of administration, the composition can be manufactured into orally administrable formulation such as tablets, hard or soft capsules, chewable tablets, powders, solutions and suspensions, or parenterally administrable formulation such as injectable solutions or suspensions, nasal lavages, etc.

For the purpose of oral administration, in preparing the present composition into orally administrable formulations such as tablets, capsules, chewable tablets, powders, solutions, suspensions, etc., binders such as gum Arabic, corn starch, microcrystalline cellulose or gelatin; excipients such as calcium phosphate or lactose; disintegrating agents such as alginic acid, corn starch or potato starch; lubricants such as magnesium stearate; sweetening agents such as sucrose or saccharin; and flavors such as peppermint, methyl salicylate or fruit flavor can be added. In case that the unit dosage form is a capsule, liquid carriers such as polyethylene glycol or fatty oil can be used in addition to the above described ones.

The injectable solution or suspension for parenteral administration can be administered parenterally, for example, subcutaneously, intravenously, intramuscularly or intraperitoneally. In general, the injectable solution or suspension can be prepared by homogeneously mixing an effective amount of the active ingredient in pharmaceutically acceptable liquid carriers such as water, saline, aqueous dextrose and its related sugar solutions, nonvolatile oil, ethanol, glycerin, polyethylene glycol, propylene glycol, etc. In addition, adjuvants such as antibacterial agents, chelating agents, buffers and preservatives can be additionally comprised.

The pharmaceutically acceptable carrier includes any adjuvants that are pharmaceutically inert, substantially non-toxic and have no inhibitory effect on the action of the active ingredient.

In addition to be prepared into pharmaceutical formulations as described above, the composition of the present invention can be also combined at a suitable amount with beverages such as conventional refreshing drink, mineral water and alcoholic beverages; chewing gums; caramels; candies; ice creams; and cookies, or can be prepared into foods or food supplements by including it in conventional health foods or health supplement foods containing vitamins, minerals and the like, or in food additives.

The composition of the present invention can be generally administered at a daily dosage of 10~1,000 mg/kg, preferably 100~500 mg/kg, and more preferably 100~200 mg/kg, as the dry extract. However, the dosage can be suitably adjusted depending upon age, sex, diet, health condition and severity of a disease of a subject, administration route, administration time, drug mixing, etc.

BEST MODE FOR CARRYING OUT THE INVENTION

Hereinafter, the present invention will be explained with reference to specific examples, but the scope of the present invention will not be limited thereby in any manner.

EXAMPLE 1

Preparation of the Composition of the Invention and Verification of its Components As dry weights of herbal medicines, 5 parts by weight of *Trionycis Carapax*, 5 parts by weight of *Raphani Semen*, 5 parts by weight of *Artemisia capillaris* Herba, 3 parts by weight of *Atractylodis Macrocephalae* Rhizoma, 3 parts by weight of *Poria cocos*, 3 parts by weight of Alismatis Rhizoma, 3 parts by weight of Atractylodis Rhizoma, 3 parts by weight of *Salvia Miltiorrhizae* Radix, 2 parts by weight of Polyporus, 2 parts by weight of Amomi Fructus, 2 parts by weight of Ponciri Fructus, 1 part by weight of Glycyrrhizae Radix and 1 part by weight of Helenii Radix were mixed together and decocted in distilled water for 2 hours. The decoction was filtered, centrifuged and lyophilized to finally obtain a dried extract (hereinafter, referred to as 'CGX' (Chunggan extract)) having the weight of approximately 11% of the dry weight of the undecocted herbal mixture.

Figure 1:
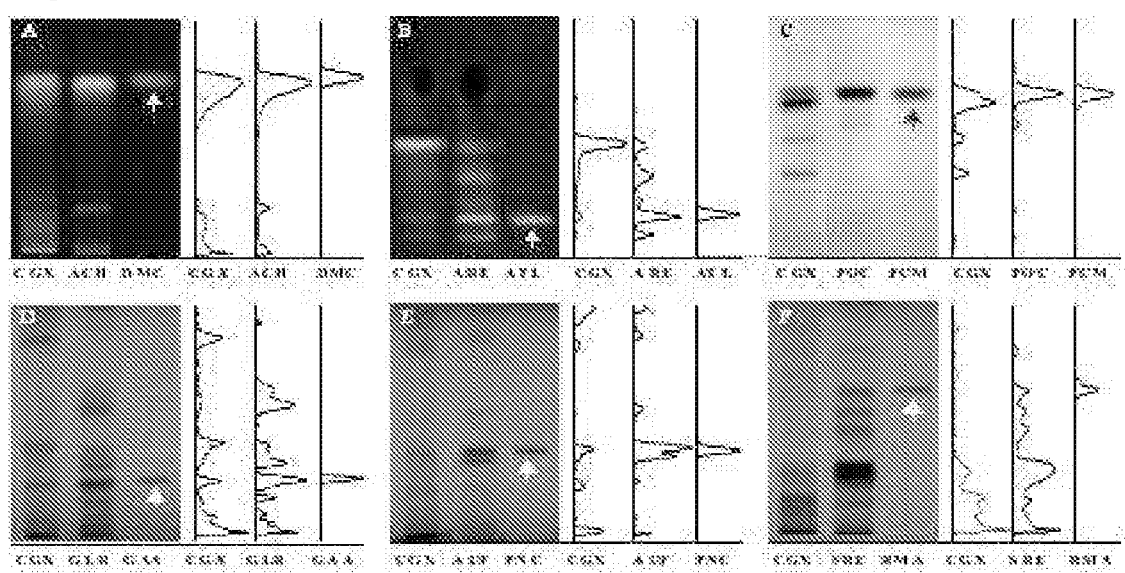
FIG. 1 is a set of photographs showing the fingerprints confirmed by using reference components of the 6 herbal medicines used in the present invention.

For the quality control of the extract, fingerprints of 6 components in the extract were confirmed by HPTLC (High Performance Thin Layer Chromatography) using reference components. The results are shown in FIG. 1. In FIG. 1, 'ACH' indicates *Artemisia capillaris* Herba, and 'DMC' indicates 6,7-dimethoxycoumarin at (A); 'ARE' indicates *Atractylodis Macrocephalae* Rhizoma, and 'ATL' indicates atractylenolide III at (B); 'POC' indicates *Poria cocos*, and 'PCM' indicates pachyman at (C); 'GLR' indicates Glycyrrhizae Radix, and 'GAA' indicates glycyrrhizinic acid ammonium salt at (D); 'AUF' indicates Ponciri Fructus, and 'PNC' indicates poncirin at (E); and, 'SRE' indicates *Salvia Miltiorrhizae* Radix, and 'RMA' indicates rosmarinic acid at (F).

EXPERIMENTAL EXAMPLE 1

Measurement of Relative Organ Weight and Histomorphological Examination of the Liver Forty SPF (specific pathogen-free) 4-week old male Wistar rats were purchased from Samtaco (Korea), and acclimated for 3 weeks and fed with commercial pellets (Samtaco, Korea) and tap water ad libitum under the 12 hour light-dark cycle with the relative humidity of 55±10% at 22±2° C. Rats with average body weight of 210±15 g were divided into 5 groups (8 rats per group, naive: no treatment, DMN 4 week: 4-week DMN treatment and sacrificed following the treatment, control: 4-week DMN treatment and 4-week water administration from the third week of DMN treatment, CGX 100 or CGX 200: 4-week DMN treatment and 4-week CGX administration from the third week of DMN treatment). DMN (dimethylnitrosoamine) diluted in saline was intraperitoneally injected at 10 mg/ml per kg for three consecutive days during each week for the DMN 4-week, control, CGX 100 and CGX 200 groups. The DMN 4-week group was sacrificed at the end of the 4-week DMN treatment. The CGX 100, CGX 200 and control groups were administered with CGX (100 or 200 mg/kg per day) or distilled water as a control daily for 4 weeks from the third week of DMN treatment.

Figure 2:
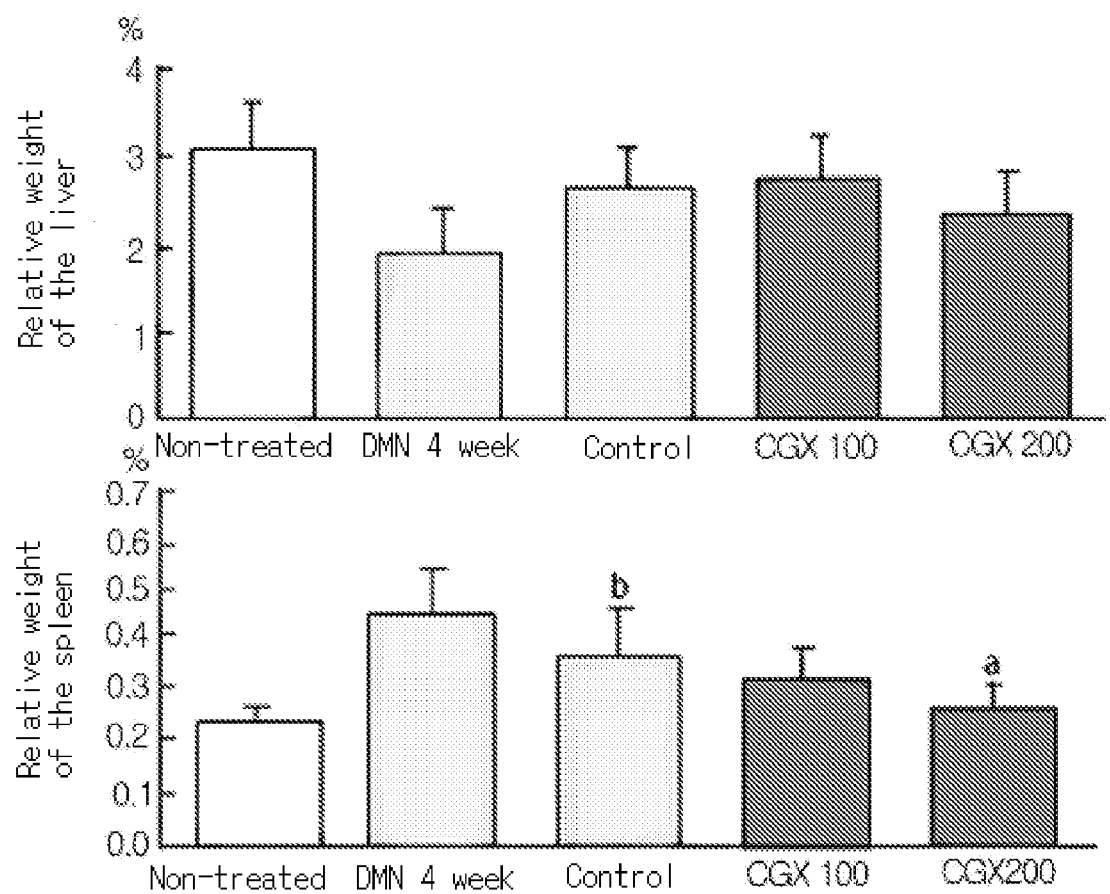
FIG. 2 is a set of graphs showing the effect of the composition of the invention on the relative organ weight of DMN (dimethylnitrosoamine)-induced chronic liver injury model in rats.

The changes in body weight for all animals were recorded weekly throughout the experimental period. The animals were sacrificed on the last day of experimentation or following the 4-week induction for the DMN 4-week group; the liver and spleen were removed and weighed. The results are shown in FIG. 2. As shown in FIG. 2, 4-week DMN treatment decreased relative liver weights compared to the control group, while it increased relative spleen weight. A 2-week cessation of DMN following the 4-week DMN treatment slightly restored these changes as seen in the control groups. These restorations were augmented by CGX administration (200 mg/kg), especially the spleen weights, compared to the control group.

For the histomorphological evaluation, a portion of liver tissue was fixed in Bouin's solution. The paraffin-embedded liver was sectioned (4-μm thickness), and Hematoxylin & eosin staining and Masson's trichome staining were performed. The representative histopathological features, such as necrosis or inflammatory cell infiltration and fibrosis, were examined under microscopy.

Figure 3A:
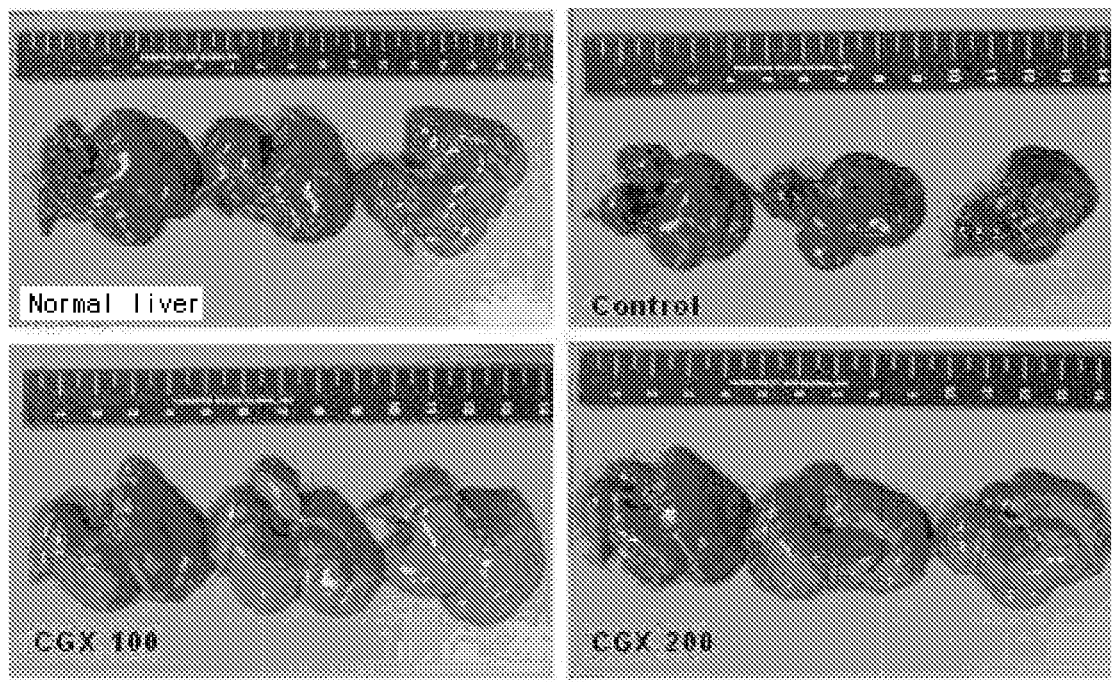
FIG. 3a is a set of photographs showing the gross appearance of the liver of the DMN-induced chronic liver injury model in rats after the treatment of the composition of the invention.
Figure 3B:
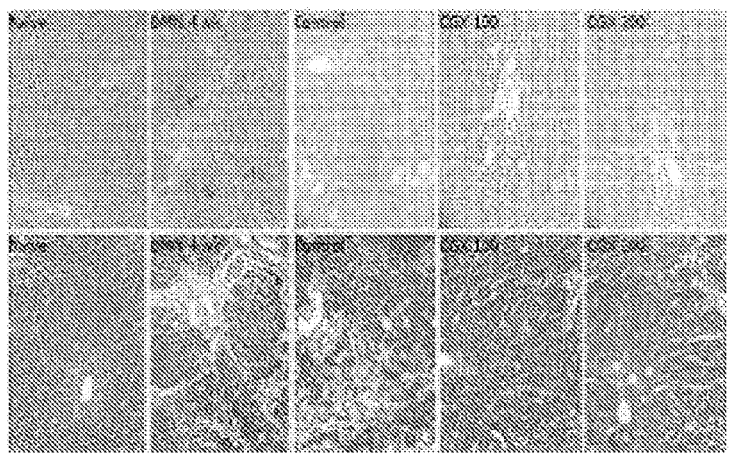
FIG. 3b is a set of photographs showing the results of histological examination of the DMN-induced chronic liver injury model in rats after the treatment of the composition of the invention.
Figure 3B:

FIG. 3*a* shows the gross appearance of the liver observed with naked eyes, and FIG. 3*b* shows the results of histological examination of the liver. As shown in FIG. 3*a*, DMN treatment appeared to shrink the liver and cause it to become blunt and congested with blood, whereas the CGX treatment reversed these changes. In addition, as shown in FIG. 3*b*, DMN treatment for 4 weeks caused severe local necrosis, inflammatory cell infiltration, hemorrhagic regions, and serious septal fibrosis, and CGX administration led to notable recovery effects (blue: fibrotic region).

EXPERIMENTAL EXAMPLE 2

Serum Biochemical Analysis

Figure 4:
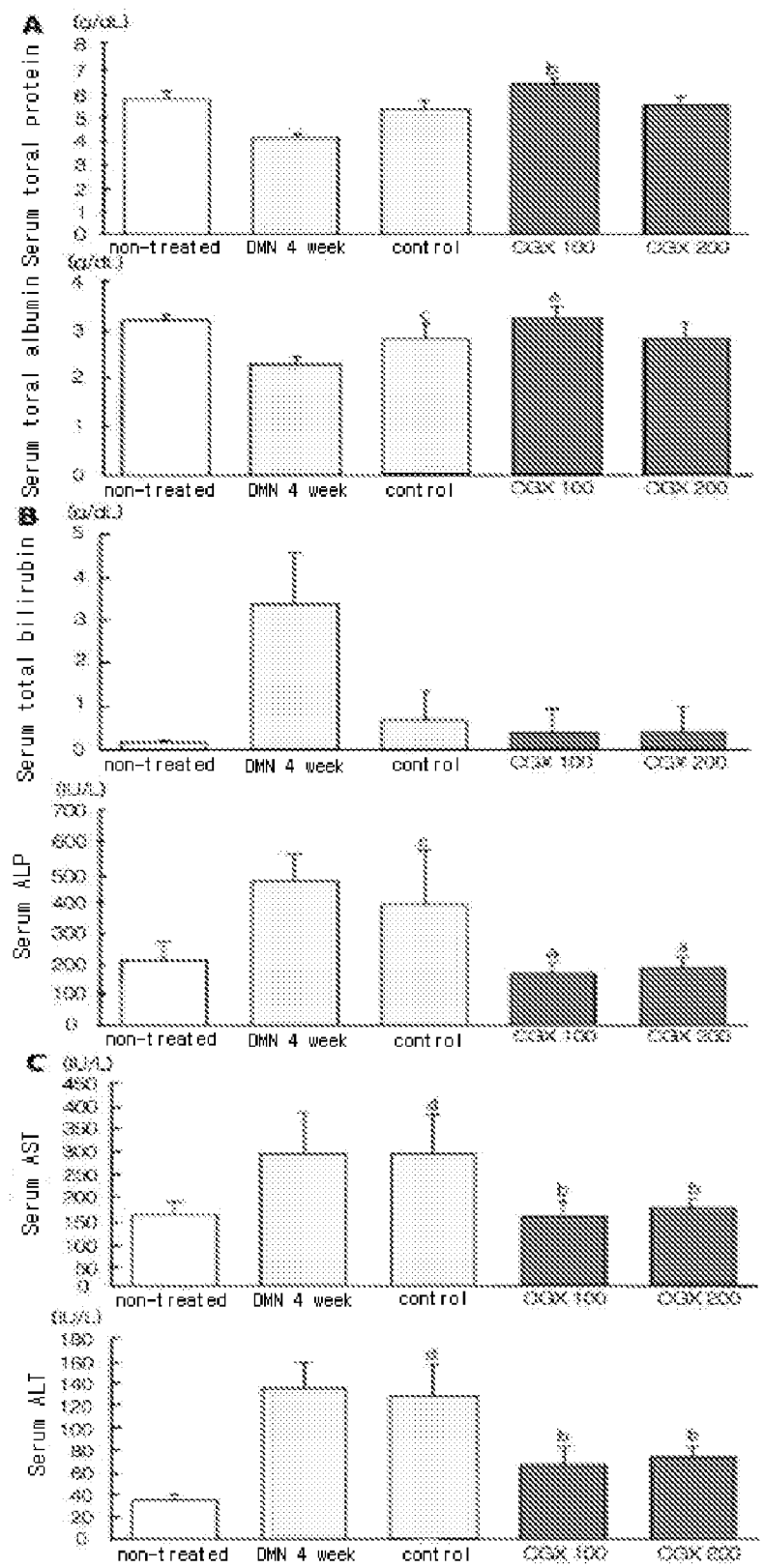
FIG. 4 is a set of graphs showing the effect of the composition of the invention on the levels of total serum protein, total bilirubin, ALP, AST and ALT of the DMN-induced chronic liver injury model in rats.

The rats were bled via abdominal aorta after ether anesthesia on the final day of the 4-week induction for the DMN 4-week group or on the final day of full experimentation for others. Sera were prepared from the blood, and the levels of total protein, albumin, total bilirubin, alkaline phosphatase (ALP), aspartate transaminase (AST), and alanine transaminase (ALT) were determined in the serum using an Auto Chemistry Analyzer (Chiron Ltd., USA). The results are shown in FIG. 4. As shown in FIG. 4, 4-week treatment with DMN induced liver dysfunction, including lowered levels of total protein and albumin along with elevated level of total bilirubin, ALP, AST, and ALT. Although these biochemical parameters were partially restored after the 2-week cessation period in the control group, AST and ALT levels still differed significantly from their normal values. CGX treatment (100 mg/kg) showed significant restoring effects on serum level of total proteins and albumin. The elevated ALP level significantly decreased with treatment by 100 mg/kg and 200 mg/kg of CGX, and the CGX treatment significantly lowered the level of AST back to nearly normal level and moderately reduced the level of ALT.

EXPERIMENTAL EXAMPLE 3

Measurement of Lipid Peroxidation and Hydroxyproline

Figure 5:
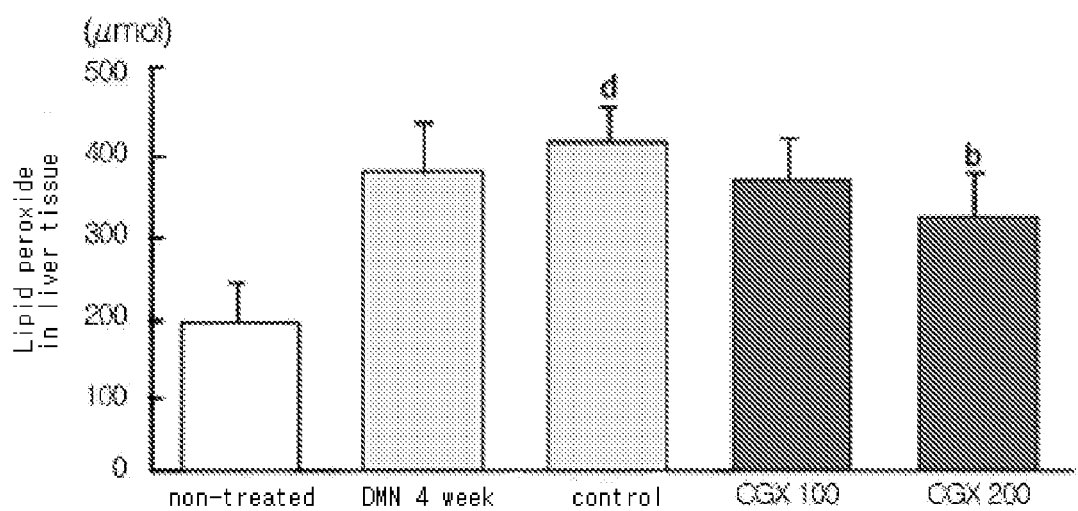
FIG. 5 is a graph showing the effect of the composition of the invention on the level of lipid peroxide in the liver of the DMN-induced chronic liver injury model in rats.

Lipid peroxidation in liver tissues was examined using the method of thiobarbitric acid reactive substances (TBARS). The concentration of TBARS was expressed as n moles of malondialdehyde (MDA) per milligram of tissue using 1.1.3.3-tetraethoxypropane (TEP) as a standard. Briefly, 0.2 g of liver tissue was homogenized in 2 ml of ice-cold 11.5 g/l KCl; then 0.13 ml of homogenate was mixed with 0.08 ml of 10 g/l phosphoric acid and 0.26 ml of 0.67% thiobarbituric acid. After heating the mixture for 45 minutes at 100° C., 1.03 ml of n-butanol was added into the mixture, followed by vigorous mixing and centrifugation at 3000 r/min for 15 minutes. The absorbance of the upper organic layer was measured at 535 and 520 nm with a spectrophotometer, and compared to the value from freshly prepared TEP as a standard. The results are shown in FIG. 5. As shown in FIG. 5, prominent lipid peroxidation occurred during the 4-week DMN treatment and progressed further during the 2-week cessation period, but 200 mg/kg CGX administration lowered it significantly.

Figure 6:
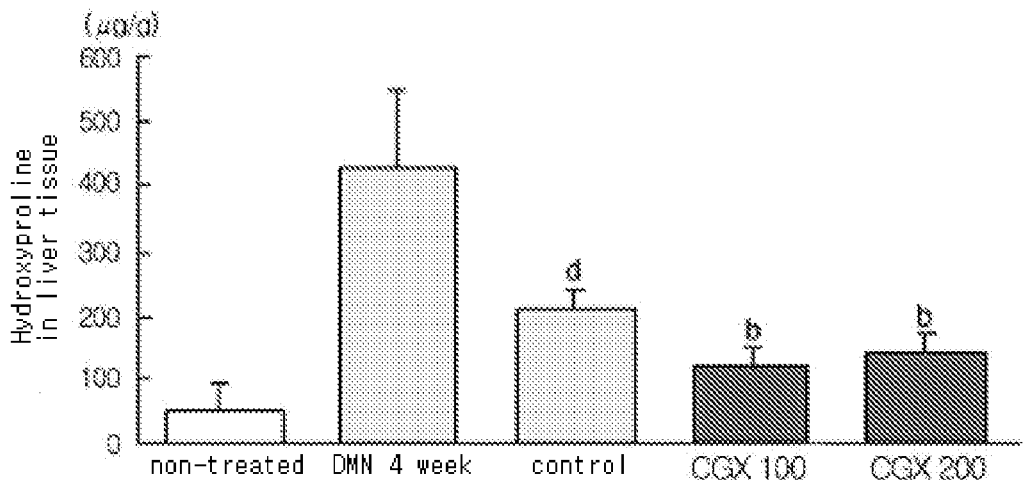
FIG. 6 is a graph showing the effect of the composition of the invention on the level of hydroxyproline in the liver of the DMN-induced chronic liver injury model in rats; and, FIG. 7 is a set of photographs showing the effect of the composition of the invention on the expression of liver fibrosis-related genes of the DMN-induced chronic liver injury model in rats.

Further, hydroxyproline assays were performed as follows. Liver tissues (0.2 g) stored at −70 ° C. were homogenized in 2 ml of 6 mol/l HCl and incubated overnight at 110° C. After filtering the acid hydrolysates using filtering paper, 50 μl of samples and standard hydroxyproline in 6 mol/l HCl were incubated to dry out the HCl; 50 μl of methanol, 1.2 ml of 500 μl/l isopropanol, and 200 ml of chloramine T solution were sequentially added to the samples, followed by incubation at room temperature for 10 minutes. Next, 1.3 ml of Ehrlich's solution was added to the mixtures and incubated further at 50° C. for 90 minutes. At the end of incubation, absorbance of the reaction mixtures was read at 558 nm. A standard curve was constructed using 0~1.0 mg/50 μl of hydroxyproline solutions. The results are shown in FIG. 6. As shown in FIG. 6, hydroxyproline rapidly increased with DMN treatment, and CGX administration significantly augmented its concentration.

EXPERIMENTAL EXAMPLE 4

Fibrosis-related Gene Expression Analysis

Total RNA was extracted from liver tissue samples with Trizol (Invitrogen, USA), RNAlater (Ambion, Inc., USA), and RNA easy column (Qiagen, Inc., USA). Complementary DNA (cDNA) was synthesized using 10 pmol of oligo dT and 10 pmol/l of random hexamer (Bioneer, Korea). After cDNA synthesis, quantitative real-time PCR was performed using SYBR green supermix reagent (Bio-Rad, USA). The following Primers were used.

① β-actin
Forward:
5'-GTGGGGCGCCCCAGGCACCA-3'      (SEQ ID NO. 1)

Reverse:
5'-CTCCTTAATGTCACGCACGATTTC-3'  (SEQ ID NO. 2)

② tumor necrosis factor-alpha (TNF-α)
Forward:
5'-CTCCCAGGTTCTCTTCAAGG-3'      (SEQ ID NO. 3)

Reverse:
5'-TGGAAGACTCCTCCCAGGTA-3'      (SEQ ID NO. 4)

③ transforming growth factor-beta (TGF-β)
Forward:
5'-TGAGTGGCTGTCTTTTGACG-3'      (SEQ ID NO. 5)

Reverse:
5'-TTCTCTGTGGAGCTGAAGCA-3'      (SEQ ID NO. 6)

④ inducible nitric oxide synthase (iNOS)
Forward:
5'-TGGTGGTGACAAGCACATTT-3'      (SEQ ID NO. 7)

Reverse:
5'-CTGAGTTCGTCCCCTTCTCC-3'      (SEQ ID NO. 8)

⑤ Fas-ligand (Fas-L)
Forward:
5'-ACTCCGTGAGTTCACCAACC-3'      (SEQ ID NO. 9)

Reverse:
5'-CAAGACTGACCCCGGAAGTA-3'      (SEQ ID NO. 10)

Reactions were performed with 12.5 μl of iQ SYBR green supermix, 1 μl of 10 pmol/l primer pairs, 10.5 μl of distilled water, and 1 μl of cDNA. Each PCR run was performed under the following conditions: initial denaturation at 95° C. for 5 minutes, 40 amplification cycles including denaturation at 95° C. for 1 minute, annealing at 58° C. for 40 seconds, and elongation at 72° C. for 40 seconds, followed by a single fluorescence measurement.

Figure 7:
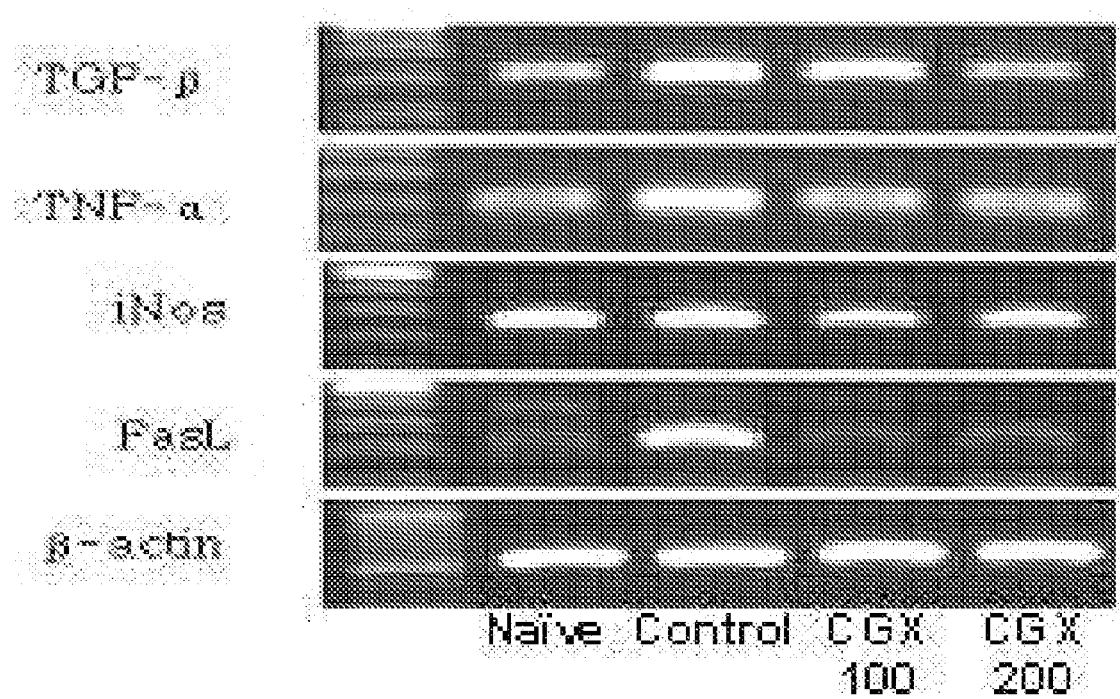

The results are shown in FIG. 7. As shown in FIG. 7, CGX treatment remarkably suppressed the expression of TNF-α, iNOS, TGF-β and Fas-L which play crucial roles on cell destruction, and inflammatory and fibrotic processes.

EXPERIMENTAL EXAMPLE 5

Toxicity Test

Forty Beagle dogs (twenty male dogs and twenty female dogs) were administered with CGX of 50 times (5 g/kg; acute toxicity test) and 4 times (400 mg/kg; subacute toxicity test) dose of the clinically recommended one (100 mg/kg). Any negative effect was examined by comparing normal and drug-administered groups with clinical symptoms, autopsy, histopathological finding, hematology, urine analysis and biochemical analysis.

In the acute toxicity test, no change in body weight, diarrhea, mortality and histopathology of main organs was observed. No drug-induced abnormality was found in histopathology, hematology, urine analysis and biochemical analysis. Therefore, CGX was considered very safe in clinical application with broad therapeutic index.

INDUSTRIAL APPLICABILITY

The composition of the present invention significantly improves bilirubin metabolic capability of the liver and hepatocellular damage, effectively inhibits lipid peroxidation, fibrosis and cirrhosis of liver tissue, and remarkably suppresses the expression of inflammation- and fibrosis-related genes, and so is extremely useful as an agent for hepatoprotection, or for prevention or treatment of liver fibrosis or cirrhosis. Furthermore, it is very safe with no toxicity on a living body.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A composition for hepatoprotection or for treating liver fibrosis or cirrhosis, said composition comprises as active ingredients, a water extract of a mixture of *Carapax Trionycis*, *Raphani Semen*, *Artemisia capillaris* Herba, *Atractylodis Macrocephalae* Rhizoma, *Poria cocos*, Alismatis Rhizoma, Atractylodis Rhizoma, *Salvia Miltiorrhizae* Radix, Polyporus, Amomi Fructus, Ponciri Fructus, Glycyrrhizae Radix and Helenii Radix.

2. The composition according to claim 1, wherein the mixture contains 2.5~7.5 parts by weight of *Carapax Trionycis*, 2.5~7.5 parts by weight of *Raphani Semen*, 2.5~7.5 parts by weight of *Artemisia capillaris* Herba, 1.5~4.5 parts by weight of *Atractylodis Macrocephalae* Rhizoma, 1.5~4.5 parts by weight of *Poria cocos,* 1.5~4.5 part by weight of Alismatis Rhizoma, 1.5~4.5 parts by weight of Atractylodis Rhizoma, 1.5~4.5 parts by weight of *Salvia Miltiorrhizae* Radix, 1~3 parts by weight of Polyporus, 1~3 parts by weight of Amomi Fructus, 1~3 parts by weight of Ponciri Fructus, 0.5~1.5 parts by weight of Glycyrrhizae Radix, and 0.5~1.5 parts by weight of Helenii Radix, as dry weights thereof.

3. The composition according to claim 2, wherein the mixture contains 5 parts by weight of *Carapax Trionycis*, 5 parts by weight of *Raphani Semen,* 5 parts by weight of *Artemisia capillaris* Herba, 3 parts by weight of *Poria cocos,* 3 parts by weight of Alismatis Rhizoma, 3 parts by weight of *Atractylodis Macrocephalae* Rhizoma, 3 parts by weight of Atractylodis Rhizoma, 3 parts by weight of *Salvia Miltiorrhizae* Radix, 2 parts by weight of Polyporus, 2 parts by weight of Amomi Fructus, 2 parts by weight of Ponciri Fructus, 1 part by weight of Glycyrrhizae Radix and 1 part by weight of Helenii Radix, as dry weights thereof.

4. The composition according to claim 1, further comprising one or more pharmaceutically or food acceptable carriers.

5. The composition according to claim 1, wherein the composition is a medicine or a health food.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 1
gtggggcgcc ccaggcacca                                          20

<210> SEQ ID NO 2
<211> LENGTH: 24
<212> TYPE: DNA
<213> ORGANISM: Artificial Sequence
<220> FEATURE:
<223> OTHER INFORMATION: Reverse primer for beta-actin -continued

```
<400> SEQUENCE: 2
ctccttaatg tcacgcacga tttc                                              24

<210> SEQ ID NO 3
<211> LENGTH: 20
<212> TYPE: DNA
<213> ORGANISM: Artificial Sequence
<220> FEATURE:
<223> OTHER INFORMATION: Forward primer for TNF-alpha

<400> SEQUENCE: 3
ctcccaggtt ctcttcaagg                                                   20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for TNF-alpha

<400> SEQUENCE: 4
tggaagactc ctcccaggta                                                   20

<210> SEQ ID NO 5
<211> LENGTH: 20
<212> TYPE: DNA
<213> ORGANISM: Artificial Sequence
<220> FEATURE:
<223> OTHER INFORMATION: Forward primer for TGF-beta

<400> SEQUENCE: 5
tgagtggctg tcttttgacg                                                   20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for TGF-beta

<400> SEQUENCE: 6
ttctctgtgg agctgaagca                                                   20

<210> SEQ ID NO 7
<211> LENGTH: 20
<212> TYPE: DNA
<213> ORGANISM: Artificial Sequence
<220> FEATURE:
<223> OTHER INFORMATION: Forward primer for iNOS

<400> SEQUENCE: 7
tggtggtgac aagcacattt                                                   20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for iNOS

<400> SEQUENCE: 8
ctgagttcgt cccctctcc                                                    20

<210> SEQ ID NO 9
<211> LENGTH: 20
```

```
-continued

<212> TYPE: DNA
<213> ORGANISM: Artificial Sequence
<220> FEATURE:
<223> OTHER INFORMATION: Forward primer for Fas-L

<400> SEQUENCE: 9
actccgtgag ttcaccaacc                                               20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for Fas-L

<400> SEQUENCE: 10
caagactgac cccggaagta                                               20
```